United States Patent
Tsumaki et al.

[11] Patent Number: 6,024,897
[45] Date of Patent: Feb. 15, 2000

[54] PROCESS FOR THE PREPARATION OF BENZYL-METAL COMPOUNDS AND PROCESS FOR THE PREPARATION OF 4-PHENYL-1-BUTENES BY THE USE OF THE SAME

[75] Inventors: Hidetoshi Tsumaki; Hidenori Matsuno, both of Shizuoka-ken, Japan

[73] Assignee: KI Chemical Industry Co., Ltd., Shizouka-ken, Japan

[21] Appl. No.: 09/011,266

[22] PCT Filed: May 29, 1997

[86] PCT No.: PCT/JP97/01843

§ 371 Date: Jan. 30, 1998

§ 102(e) Date: Jan. 30, 1998

[87] PCT Pub. No.: WO97/45433

PCT Pub. Date: Dec. 4, 1997

[30] Foreign Application Priority Data

May 30, 1996 [JP] Japan ................................. 8-136608
Jul. 29, 1996 [JP] Japan ................................. 8-199128

[51] Int. Cl.$^7$ ................ C07F 1/00; C07F 1/02; C07F 1/04; C07F 1/06
[52] U.S. Cl. ............... 260/665 R; 585/452; 585/453; 568/626
[58] Field of Search ............. 260/665 R; 585/452, 585/453; 568/626

[56] References Cited

U.S. PATENT DOCUMENTS

| | | | |
|---|---|---|---|
| 3,953,535 | 4/1976 | Shima et al. .......................... | 585/438 |
| 4,006,187 | 2/1977 | Kamienski et al. .................. | 260/665 R |
| 4,018,840 | 4/1977 | Iwata et al. .......................... | 585/438 |
| 4,084,061 | 4/1978 | Kanazawa et al. ................... | 560/105 |
| 4,155,942 | 5/1979 | Hara et al. . | |
| 4,709,109 | 11/1987 | Sperling et al. ..................... | 585/438 |
| 5,030,784 | 7/1991 | Slaugh . | |
| 5,329,058 | 7/1994 | Shimada et al. ..................... | 585/452 |
| 5,523,504 | 6/1996 | Itoh ..................................... | 585/452 |
| 5,659,097 | 8/1997 | Fushimi et al. ...................... | 585/438 |

FOREIGN PATENT DOCUMENTS

| | | |
|---|---|---|
| 48-75551 | 10/1973 | Japan . |
| 3294271 | 12/1991 | Japan . |
| 9157191 | 6/1997 | Japan . |

OTHER PUBLICATIONS

J. Chem. Soc., 1975 –1979(1950).
J. Org. Chem., 26:3723–3729 (1961).
J. Oranomet. Chem., 2:431–433 (1964).
Organometallics, 4: 2117–2121 (1985).
Angew. Chem. Int. Ed. Engl., 32:1501–1523 (1993).
J. Am. Chem. Soc., 62:1514–1519 (1940).
J. Am. Chem. Soc., 55, 699–702 (1933).

*Primary Examiner*—Paul F. Shaver
*Attorney, Agent, or Firm*—Birch, Stewart, Kolasch & Birch, LLP

[57] ABSTRACT

There is disclosed a method of preparing benzyl metal compounds represented by general formula (2), comprising reacting a phenyl metal compound represented by general formula (1) with toluene, in the presence of a catalytic amount of amine. According to this method, benzyl metal compounds can be prepared at a high yield, and in an industrially advantageous manner. Further, there is also disclosed a method of preparing 4-phenyl-1-butenes, comprising reacting the benzyl metal compound obtained in the method, with an allyl halide.

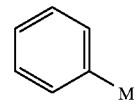

(1)

wherein M represents an alkali metal,

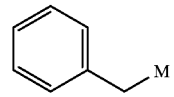

(2)

wherein M has the same meaning as the above.

12 Claims, No Drawings

PROCESS FOR THE PREPARATION OF BENZYL-METAL COMPOUNDS AND PROCESS FOR THE PREPARATION OF 4-PHENYL-1-BUTENES BY THE USE OF THE SAME

This application is the national phase under 35 U.S.C. §371 of prior PCT International Application No. PCT/JP 97/01843 which has an International filing date of May 29, 1997 which designated the United States of America, the entire contents of which are hereby incorporated by reference.

TECHNICAL FIELD

The present invention relates to a method of preparing benzyl metal compounds that are useful as a synthetic intermediate.

Further, the present invention relates to a novel method of preparing 4-phenyl-1-butenes that are useful as a synthetic intermediate of agricultural chemicals and medicines. More specifically, the present invention relates to a method of preparing 4-phenyl-1-butenes, in which the above-described method of preparing benzyl metal compounds is used.

BACKGROUND ART

Benzyl metal compounds are important synthetic intermediates for construction of a carbon skeleton. Hitherto, there are many known synthesis methods of such compounds, as exemplified below. (1) A method in which a benzyl ether is reacted with lithium, to give benzyl lithium (J. Org. Chem., 26, 3723 (1961)); (2) A method in which benzyl halides are reacted with metal zinc or cadmium, to give benzyl zinc halides or benzyl cadmium halides (Compt. Rend., 245, 2054 (1957)); (3) A method in which, first, a Grignard reagent prepared from benzyl halides and metal magnesium is converted to a benzyl mercury compound or a benzyl tin compound, and then the resultant compound is treated with an alkyl lithium, to give benzyl lithium (J. Organomet. Chem., 2, 431 (1964)); (4) A method in which toluene is reacted with an alkyl lithium, in the presence of a specific ligand (Organometallics, 4, 2117 (1985)); (5) A method in which an alkyl lithium compound is reacted with another metal alkoxide, and then the resultant alkyl metal compound is reacted with toluene (Angew. Chem. Int. Ed. Engl., 32, 1501 (1993)); (6) A method in which phenyl sodium is reacted with toluene, under heat reflux (J. Am. Chem. Soc., 62, 1514 (1940)); (7) A method in which phenyl sodium is reacted with toluene, in the presence of tetrahydrofuran, at room temperature (JP-A-48-75551 ("JP-A" means unexamined published Japanese patent application)).

However, all of these methods have some respective problems. That is, in the method (1), only 1 equivalent of benzyl lithium can be generated from 2 equivalents of expensive lithium. In the method (2), the yield is low. The route of the method (3), via a benzyl mercury compound or a benzyl tin compound, is to remove dibenzyl (Wurtz coupling product), which is a by-product at the Grignard reaction, but the method (3) cannot be used in industrial production because harmful heavy metal wastes are discharged. The methods (4) and (5) are not economically profitable, because an expensive alkyl lithium compound is used, and moreover it is necessary to add a ligand that is used to accelerate the reaction, in an amount of not less than 1 equivalent. In the method (6), the reaction of phenyl sodium with toluene is so slow at room temperature that the operation of heat reflux is necessary, as well as that the heat reflux also causes the problem that tar is generated due to thermal decomposition of phenyl sodium. The method (7) was developed to attempt to overcome the drawbacks of the method (6). Consequently the method (7) has an advantage that the reaction can be carried out at room temperature, but actually this method is not suitable for industrial production, from a viewpoint of separation and recovery of a solvent, because it is necessary to add water-soluble tetrahydrofuran to phenyl sodium, in an amount of 20 to 300 wt % based on phenyl sodium.

On the other hand, examples of a method of preparing 4-phenyl-1-butenes include (a) a method in which benzyl magnesium halides are reacted with allyl halides (e.g. J. Am. Chem. Soc., 55, 699 (1933)), (b) a method in which allyl magnesium halides are reacted with benzyl halides (e.g. Bull. Soc. Chim. Fr., 43, 1326 (1928)), (c) a method in which phosphorusylides are reacted with carbonyl compounds according to the Wittig reaction (e.g. JP-A-3-294271), (d) a method in which phenethyl magnesium halides are reacted with vinyl halides, in the presence of a nickel catalyst (e.g. U.S. Pat. No. 5,030,784), and (e) a method in which allyl halides are reacted with benzyl sodium that was obtained by reacting phenyl sodium with toluene under heat reflux (e.g. J. Chem. Soc., 1975 (1950)).

However, in the methods (a) and (b), synthesis of the Grignard reagent itself is difficult, due to competition with the Wurtz coupling. In the methods (c) and (d), expensive catalysts are used, and a great deal of effort is required to separate and purify the products. Consequently, it is difficult to say that these methods are not satisfactory for industrial practice. The method (e) necessitates the operation of heat reflux in order to give benzyl sodium, and at this time thermal decomposition of phenyl sodium occurs, so that reduction of the yield is unavoidable. For example, the yield of 4-phenyl-1-butene that is given by reacting with allyl chloride is only about 51 to 72%.

The present invention was made in order to solve the above-described problems, and an object of the present invention is to provide a novel method of preparing benzyl metal compounds.

Further, another object of the present invention is to provide a method that can prepare 4-phenyl-1-butenes from benzyl metal compounds, in which the benzyl metal compounds are prepared, at a high purity and a high yield, by the use of relatively easily available raw materials, catalysts, and the like, without heat reflux and the like.

Other and further objects, features, and advantages of the invention will appear more fully from the following description.

DISCLOSURE OF INVENTION

In this situation, the inventors of the present invention studied a reaction of phenyl metal compounds with toluene, and as a result it was found that, when a catalytic amount of amines exists, metal-hydrogen exchange reaction very rapidly undergoes, and benzyl metal compound can almost quantatively be given. This finding led to complete the present invention.

That is, the present invention provides;
(1) A method of preparing benzyl metal compounds represented by general formula (2), comprising reacting a phenyl metal compound represented by general formula (1) with toluene, in the presence of a catalytic amount of amine (preferably a secondary amine, or a tertiary amine):

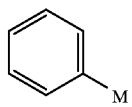

wherein M represents an alkali metal (preferably sodium, or potassium),

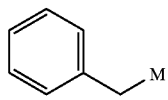

wherein M has the same meaning as the above; and (2) A method of preparing 4-phenyl-1-butenes represented by general formula (4):

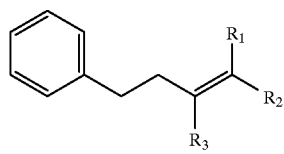

wherein $R_1$, $R_2$, and $R_3$, which are the same or different, each represent a hydrogen atom, an alkyl group, or an alkoxyalkyl group, comprising reacting a phenyl metal compound represented by general formula (1):

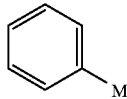

wherein M represents an alkali metal (preferably sodium, or potassium), with toluene, in the presence of amine (preferably a secondary amine, or a tertiary amine), to give a benzyl metal compound represented by general formula (2):

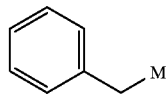

wherein M has the same meaning as in general formula (1), and then reacting the resultant benzyl metal compound with an allyl halide represented by general formula (3):

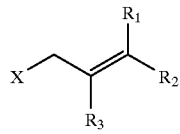

wherein X represents a halogen atom, and $R_1$, $R_2$, and $R_3$ each have the same meanings as in general formula (4).

BEST MODE FOR CARRYING OUT THE INVENTION

Methods for carrying out the present invention are specifically explained below.

The above-mentioned phenyl metal compounds of general formula (1) for use in the present invention can be easily obtained by a usual preparation method; that is, for example, a method in which chlorobenzene or the like is reacted with a dispersion of alkali metal particles (for example, sodium or potassium particles). The solvent for use in this reaction is preferably inactive to the reaction, as exemplified by octane, benzene, and toluene. In the present invention, toluene is most preferable, from the point of view that it can also be used as a reactant in the subsequent step. The amount of toluene to be used is preferably from 2 to 30 times the amount of chlorobenzene, by weight.

In the preparation of the benzyl compound of general formula (2), comprising a reaction of the phenyl metal compounds with toluene according to the method of the present invention, the reaction may be carried out with no solvent (the term "no solvent" means no solvent, except for the above-described toluene, is used). At this time, the amount of toluene to be used is preferably from 1:2 to 1:30, more preferably from 1:3 to 1:10, in terms of the reaction molar ratio of a phenyl metal compound and toluene.

In general formulae (1) and (2), M represents an alkali metal, preferably sodium or potassium.

This reaction is carried out in the presence of an amine catalyst. The amount of the coexistent amines is usually from 0.1 to 20 mol %, preferably from 1 to 10 mol %, of the phenyl metal compounds. If the amount of the amines to be used is too small, the reaction rate reduces, so that it unavoidably takes a long time to terminate the reaction, whereas an excess amount of the amines is not economical. The amines are preferably secondary amines and tertiary amines. Examples of the amines include diethylamine, di-n-propylamine, diisopropylamine, di-n-butylamine, diisobutylamine, di-sec-butylamine, di-n-pentylamine, di-n-hexylamine, dicyclohexylamine, di-n-octylamine, N-isopropylhexylamine, N-isopropylcyclohexylamine, N-isopropylbenzylamine, pyrrolidine, 2,5-dimethylpyrrolidine, 2,5-dimethyl-3-pyrroline, piperidine, 2,6-dimethylpiperidine, 2,2,6,6-tetramethylpiperidine, 2,2,6,6-tetramethyl-4-piperidinol, morpholine, N,N,N',N'-tetramethyldiaminomethane, N,N,N',N'-tetramethylethylenediamine, N,N,N',N'-tetramethyl-1,3-diaminopropane, N,N,N',N'-tetramethyl-1,4-diaminobutane, N,N,N',N'-tetramethyl-2-butene-1,4-diamine, N,N,N',N'-tetramethyl-1,6-diaminohexane, N,N,N',N'-tetramethyl-1,8-naphthalenediamine, and N,N,N',N",N"-pentamethyldiethylenetriamine. More preferred of these amines are diisopropylamine, di-sec-butylamine, dicyclohexylamine, N-isopropylhexylamine, N-isopropylcyclohexylamine, 2,5-dimethylpyrrolidine, 2,6-dimethylpiperidine, 2,2,6,6-tetramethylpiperidine, N,N,N',N'-tetramethylethylenediamine, and N,N,N',N",N"-pentamethyldiethylenetriamine.

Of these amines, secondary amines are more preferable. Specifically, the above-described examples of the secondary amines are preferably used.

A preferable combination in the present invention is the embodiment in which the amines are secondary amines or tertiary amines, and the alkali metal represented by M in general formulae (1) and (2) is sodium or potassium. The embodiment in which the amines are secondary amines, and the alkali metal is sodium or potassium, is more preferable.

The amines for use in the present invention are added alone, or as a diluent solution with almost the same amount of the solvent as amines. Examples of this solvent include solvents that can be used for preparing the phenyl metal compounds represented by general formula (1). The method for adding, by dropping, is not limited in particular. The reaction temperature is usually from 0 to 40° C., preferably from 15 to 30° C., and therefore heating is not necessary in particular. The reaction time of from 1 to 5 hours under such a temperature condition, is usually adequate. Even if the reaction time is longer than the above upper limit, no particular bad effect is caused.

This reaction completes under such a moderate condition as mentioned above. Consequently, the phenyl metal compound is prevented from thermal decomposition, which results in obtaining of the benzyl metal compound at a high yield.

As mentioned above, in the conventional method (4), in which alkyl lithium is reacted with toluene, it is necessary to add a ligand to accelerate the reaction, in an amount of not less than 1 equivalent. Further, in the conventional method (7) in which phenyl sodium is reacted with toluene, it is required to add a large amount of tetrahydrofuran, which is difficult to recover. The present invention has economic advantages, as compared to these conventional methods, because the amines for use in the present invention are adequate in an extremely small amount, or differently stated, in a catalytic amount, and also they can be easily recovered by such an operation as extraction, if necessary. Particularly, the use of secondary amines exhibits a considerable reaction rate even at room temperature. As a result, the amount of secondary amines to be used can be further reduced, as compared to the catalytic amount of tertiary amines, so that the use of secondary amines is satisfactory for industrial production method.

The benzyl metal compounds thus obtained easily react with moisture in air, so that it is difficult to isolate the compounds. For this reason, formation of the benzyl metal compounds can be identified by reacting them with another reagent, to convert them to another compounds. For example, there are already well-known reactions of the benzyl metal compounds with such electrophilic reagents as trimethylchlorosilane (e.g. J. Org. Chem., 46, 265 (1981)), butyl bromide (e.g. J. Chem. Soc., 1975 (1950)), and the like. Consequently, benzyltrimethylsilane, pentylbenzene, and the like can be obtained by the above-described reaction at high yields, respectively. Further, by the reaction of the benzyl metal compounds with carbon dioxide (e.g. J. Am. Chem. Soc., 62, 1514 (1940)), phenylacetic acid, which is important as a raw material of agricultural chemicals and medicines, can be prepared at a high yield. The formation of the benzyl metal compounds can be identified by these methods.

Similarly, the formation of the benzyl metal compound as an intermediate can also be identified by identifying 4-phenyl-1-butenes formed as a result of a reaction of the benzyl metal compound obtained in the above manner, with allyl halides.

Next, a reaction of the benzyl metal compounds of general formula (2) thus obtained, with allyl halides of general formula (3), is explained below.

In general formula (3), X represents a halogen atom, e.g. a chlorine atom or a bromide atom; $R_1$, $R_2$, and $R_3$, which are the same or different, represent a hydrogen atom, an alkyl group (saturated or unsaturated, linear or branched chain alkyl groups having preferably 18 or less carbon atoms, more preferably 1 to 10 carbon atoms, with examples including methyl, ethyl, propyl, butyl, pentyl, and 3,7-dimethyl-2,6-octadienyl groups), or an alkoxyalkyl group (saturated or unsaturated, linear or branched chain alkoxyalkyl groups having preferably 2 to 15 carbon atoms, more preferably 2 to 8 carbon atoms, whose alkoxyl moiety may be aliphatic or aromatic, with examples including methoxymethyl, ethoxymethyl, phenoxymethyl, and benzyloxymethyl groups).

Specific preferable examples of the allyl halides of general formula (3) include allyl chloride, allyl bromide, methallyl chloride, methallyl bromide, crotyl chloride, crotyl bromide, prenyl chloride, prenyl bromide, 1-chloro-2-pentene, 1-chloro-2-hexene, 1-chloro-2-octene, 1-chloro-2-nonene, 1-chloro-2-methyl-2-butene, 1-bromo-4-methoxy-2-methyl-2-butene, 1-bromo-4-ethoxy-2-methyl-2-butene, 1-bromo-4-phenoxy-2-methyl-2-butene, 1-bromo-4-benzyloxy-2-methyl-2-butene, and geranyl chloride. More preferred are allyl chloride, methallyl chloride, crotyl chloride, prenyl chloride, and 1-bromo-4-methoxy-2-methyl-2-butene.

The amount of the allyl halides of general formula (3) to be used is usually in the range of from 0.7 to 1.5 times, preferably from 0.9 to 1.1 times, of the molar amount of the benzyl metal compounds represented by general formula (2). The reaction temperature is usually in the range of from −20° C. to 50° C., preferably from −10° C. to 30° C. The method for adding, by dropping, allyl halides is not limited in particular, and the allyl halides may be added to the benzyl metal compounds represented by general formula (2) over a suitable period of time. At that time, the allyl halides of general formula (3), if necessary, may be diluted and dissolved with the same solvent used in the reaction of the preceding step.

After the reaction, a reaction mixture is worked up by means of distillation, crystallization, and the like, to give 4-phenyl-1-butenes desired.

In the present invention, each of the steps may be carried out in a separate reaction vessel, or alternatively in one reaction vessel (one pot).

EXAMPLES

The present invention will be explained below in more detail by means of the following examples, but they are not intended to restrict the scope of the present invention.

Example 1

A toluene (2 g) solution containing 0.21 g of diisopropyl amine (2.07 mmol, 2 mol % (mol % on the basis of phenyl sodium, which is also used hereinafter in the same meaning)) was added to phenyl sodium, which had been prepared by reacting 5.0 g (0.217 mol) of sodium dispersion and 11.6 g (0.103 mol) of chlorobenzene in 50 g of toluene (phenyl sodium was formed at the yield of about 100%, hereinafter the same as the above), at room temperature (about 20° C.), and then the reaction mixture was stirred for 2 hours. As the reaction proceeded, slight generation of heat occurred and a dark violet-colored slurry turned to a greenish brown-colored slurry. After that, an excess amount of dry ice was cast into the resultant slurry, little by little, keeping the reaction temperature at the range of from −10° C. to 0° C., and then the slurry was subjected to hydrolysis with 30 ml of water. The resulting aqueous layer was fractionated, and then it was washed with 10 g of toluene. After that, the aqueous solution was subjected to acid crystallization with concentrated hydrochloric acid, to give 13.2 g of phenylacetic acid (0.097 mol, 94.2% (the yield based on chlorobenzene, which will be used hereinafter in the same meaning), m.p. 75 to 77° C.) as white crystals. At that time, almost no benzoic acid derived from phenyl sodium was detected. This fact indicates that phenyl sodium was almost quantitatively changed to benzyl sodium by the presence of the diisopropylamine catalyst.

Example 2

A toluene (5 g) solution containing 0.87 g (8.60 mmol, 2 mol %) of diisopropylamine was added to phenyl sodium, which had been prepared by reacting 20.0 g (0.870 mol) of sodium dispersion and 48.0 g (0.426 mol) of chlorobenzene in 160 g of tolunene, at room temperature, and then the reaction mixture was stirred for 2 hours. To the resultant greenish brown slurry, 46.3 g (0.426 mol) of trimethylchlorosilane was added, dropwise, keeping the reaction temperature in the range of from 15 to 20° C., and then the reaction mixture was subjected to hydrolysis with 100 ml of water. After the separated organic layer was washed with water three times, the thus-obtained organic solution was subjected to gas chromatography analysis. As a result, it was found that benzyltrimethylsilane was produced, at the yield of 98.5%, while the yield of phenyltrimethylsilane was not more than 0.5%. This fact indicates that phenyl sodium was almost quantitatively converted to benzyl sodium. Further, a solvent was distilled off from the obtained organic layer, and then the remaining slightly yellowish oil was distilled under reduced pressure, to give 65.5 g of benzyltrimethylsilane (0.399 mol, 93.7%, b.p. 120 to 122° C./100 mmHg).

Example 3

The procedures were carried out in the same manner as in Example 2, except that a toluene (5 g) solution containing 3.85 g (21.3 mmol, 5 mol %) of dicyclohexylamine was added, dropwise, to phenyl sodium, which had been prepared by reacting 20.0 g (0.870 mol) of sodium dispersion and 48.0 g (0.426 mol) of chlorobenzene in 160 g of toluene, at room temperature, and then the reaction mixture was stirred for 5 hours, to give benzyltrimethylsilane, at the reaction yield of 98.0%.

Example 4

The procedures were carried out in the same manner as in Example 2, except that a toluene (8 g) solution containing 0.60 g (4.3 mmol, 1 mol %) of 2,2,6,6-tetramethylpiperidine was added, dropwise, to phenyl sodium, which had been prepared by reacting 20.0 g (0.870 mol) of sodium dispersion and 48.0 g (0.426 mol) of chlorobenzene in 160 g of toluene, at room temperature, and then the reaction mixture was stirred for 1 hour, to give benzyltrimethylsilane, at the reaction yield of 99.0%.

Example 5

The procedures were carried out in the same manner as in Example 2, except that a toluene (10 g) solution containing 1.22 g (10.5 mmol, 5 mol %) of N,N,N',N'-tetramethylethylenediamine was added to phenyl sodium, which had been prepared by reacting 9.9 g (0.430 mol) of sodium dispersion and 23.7 g (0.211 mol) of chlorobenzene in 200 g of toluene, at room temperature, and then the reaction mixture was stirred for 2 hours, to give benzyltrimethylsilane, at the reaction yield of 98.7%.

Example 6

The procedures were carried out in the same manner as in Example 2, except that a toluene (7 g) solution containing 3.69 g (21.3 mmol, 5 mol %) of N,N,N',N'',N''-pentamethylethylenetriamine was added to phenyl sodium, which had been prepared by reacting 20.0 g (0.870 mol) of sodium dispersion and 48.0 g (0.426 mol) of chlorobenzene in 160 g of toluene, at room temperature, and then the reaction mixture was stirred for 1 hour, to give benzyltrimethylsilane, at the reaction yield of 99.2%.

Comparative Example 1

In 180 g of toluene, 22.4 g (0.974 mol) of sodium dispersion was reacted with 53.8 g (0.478 mol) of chlorobenzene, to give phenyl sodium. The resultant toluene slurry of phenyl sodium was stirred for 8 hours at room temperature. A portion of the reaction solution was taken, and then the same was reacted with an excess amount of trimethylchlorosilane, followed by gas chromatography analysis. As a result, it was found that the yield of benzyltrimethylsilane was 16.3%.

Example 7

A toluene (20 g) solution containing 2.58 g (0.025 mol, 2 mol %) of diisopropylamine was added to phenyl sodium, which had been prepared by reacting 60.0 g (2.610 mol) of sodium dispersion and 144.0 g (1.279 mol) of chlorobenzene in 800 g of toluene, at room temperature (about 20° C.), and then the reaction mixture was stirred for 2 hours. To the resultant greenish brown slurry was added a toluene (40 g) solution containing 98.0 g (1.280 mol) of allyl chloride, keeping the reaction temperature in the range of from −10° C. to 0° C., and then the reaction mixture was allowed to stand, for aging, for 1 hour at room temperature. After the reaction was completed, the reaction mixture was subjected to hydrolysis with 250 ml of sulfuric acid (5%) in the range of 5 to 20° C., and then the resultant solution was allowed to stand, then it was separated. The separated organic layer was washed with 200 ml of water twice, followed by gas chromatography analysis. It was identified that 4-phenyl-1-butene was given, at the yield of 96.4%. Further, the organic layer was condensed by atmospheric distillation, and the residue was further subjected to distillation under reduced pressure at 106° C./105 mmHg, to give 148.0 g of 4-phenyl-1-butene (1.119 mol, yield 87.5% on the basis of chlorobenzene. The term "yield" is hereinafter used in the same meaning as the above), followed by gas chromatography, for purity testing. As a result, it was found that the purity of 4-phenyl-1-butene was 98.7%.

Comparative Example 2

In 220 g of toluene, 20.3 g (0.883 mol) of sodium dispersion was reacted with 46.5 g (0.413 mol) of chlorobenzene, to prepare phenyl sodium. The resultant toluene slurry was stirred for 2.5 hours under heat reflux. The thus-obtained black slurry was cooled, and then a toluene (40 g) solution containing 31.6 g (0.413 mol) of allyl chloride was added to the cooled slurry, keeping the reaction temperature in the range of from −10° C. to 0° C., and then the reaction mixture was allowed to stand, for aging, for 30 minutes at room temperature. After the reaction was completed, the reaction mixture was subjected to hydrolysis with 350 ml of water in the range of 5 to 20° C., and then the resultant organic layer was washed with 300 ml of water twice, according to a usual manner. Toluene was removed therefrom by atmospheric distillation, and the residual orange oil was subjected to distillation under reduced pressure in the same manner as in Example 7. As a result, 39.4 g (0.298 mol, yield 72.2%) of 4-phenyl-1-butene was given (purity 98.3%), and 6.3 g of a residue remained.

INDUSTRIAL APPLICABILITY

According to the method of the present invention, benzyl metal compounds can be prepared, at a high efficiency and a high yield, from industrially available phenyl metal compounds by means of simple operations, without the use of heavy metal compounds and the like, as in the conventional methods.

Further, according to the method of the present invention, benzyl metal compounds can be prepared under mild conditions, without carrying out heat reflux and the like. Consequently, thermal decomposition of phenyl metal compounds does not occur, and therefore desired 4-phenyl-1-butenes can be given at a high purity and a high yield, from the benzyl metal compounds that was prepared according to the method of the present invention. Further, the method of the present invention exhibits such excellent actions/effects of the invention that neither reactants that are difficult to be synthesized, nor expensive catalysts, are necessary, and that all the steps can be carried out in one pot, and further that separation and purification of the product are relatively easy. Consequently, the method of the present invention is preferable for implementation on an industrial scale.

Having described our invention as related to the present embodiments, it is our intention that the invention not be limited by any of the details of the description, unless otherwise specified, but rather be construed broadly within its spirit and scope as set out in the accompanying claims.

We claim:

1. A method of preparing benzyl metal compounds represented by general formula (2), comprising reacting a phenyl metal compound represented by general formula (1) with toluene, in the presence of a catalytic amount of amine:

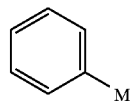 (1)

wherein M represents an alkali metal,

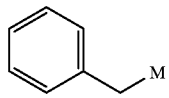 (2)

wherein M has the same meaning as the above.

2. The method of preparing benzyl metal compounds as claimed in claim 1, wherein the amine is a secondary amine.
3. The method of preparing benzyl metal compounds claimed in claim 1, wherein the amine is a tertiary amine.
4. The method of preparing benzyl metal compounds as claimed in claim 1, wherein M is sodium or potassium.
5. The method of preparing benzyl metal compounds as claimed in claim 4, wherein M is sodium.
6. The method of preparing benzyl metal compounds as claimed claim 1, wherein an amount of the amine to be used is 0.1 to 20 mol % to the phenyl metal compound.
7. A method of preparing 4-phenyl-1-butenes represented by general formula (4):

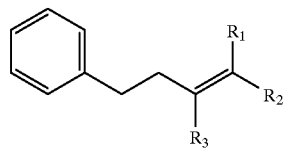

wherein $R_1$, $R_2$, and $R_3$, which are the same or different, each represent a hydrogen atom, an alkyl group, or an alkoxyalkyl group, comprising reacting a phenyl metal compound represented by general formula (1):

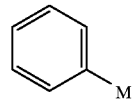

wherein M represents an alkali metal, with toluene, in the presence of amine, to give a benzyl metal compound represented by general formula (2):

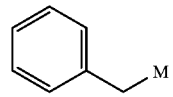

wherein M has the same meaning as in general formula (1), and then reacting the resultant benzyl metal compound with an allyl halide represented by general formula (3):

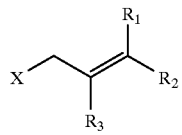

wherein X represents a halogen atom, and $R_1$, $R_2$, and $R_3$ each have the same meanings as in general formula (4).

8. The method of preparing 4-phenyl-1-butenes as claimed in claim 7, wherein the amine for the preparation of the benzyl metal compound is a secondary amine.
9. The method of preparing 4-phenyl-1-butenes as claimed in claim 7, wherein the amine for the preparation of the benzyl metal compound is a tertiary amine.
10. The method preparing 4-phenyl-1-butenes as claimed in claim 7, wherein M is sodium or potassium.
11. The method of preparing 4-phenyl-1-butenes as claimed in claim 10, wherein M is sodium.
12. The method of preparing benzyl metal compounds as claimed in claim 7, wherein an amount of the amine to be used for the preparation of the benzyl metal compound is 0.1 to 20 mol % to the phenyl metal compound.

* * * * *